United States Patent [19]

Kuehn

[11] 4,136,694
[45] Jan. 30, 1979

[54] SEPARABLE INTEGRAL DONOR TUBE UTILIZING AN INTEGRAL PLASTIC MEMBER WITH TUBE CLAMP

[75] Inventor: Robert L. Kuehn, Newport Beach, Calif.

[73] Assignee: Baxter Travenol Laboratories, Inc., Deerfield, Ill.

[21] Appl. No.: 805,364

[22] Filed: Jun. 10, 1977

[51] Int. Cl.$^2$ ............................................. A61M 05/00
[52] U.S. Cl. ............................. 128/214 D; 128/214.2; 251/9; 251/342
[58] Field of Search ........... 128/214 R, 214 C, 214 D, 128/214.2, 274; 251/4.7, 9, 342

[56] References Cited

U.S. PATENT DOCUMENTS

| | | | |
|---|---|---|---|
| 2,825,333 | 3/1958 | Broman | 128/214 R |
| 3,127,892 | 4/1964 | Bellamy | 128/214.2 |
| 3,217,710 | 11/1965 | Beall et al. | 128/214.2 |
| 3,342,179 | 9/1967 | Ellmann | 128/214.2 |
| 3,612,474 | 10/1971 | Strohl | 128/214 R X |

Primary Examiner—Dalton L. Truluck
Attorney, Agent, or Firm—Henry W. Collins; Paul C. Flattery; Garrettson Ellis

[57] ABSTRACT

A blood tube communicating with a blood bag includes means for parting the blood tube, and exposing an internally mounted needle carried by and communicating with the blood tube for penetrating a closure of a sample tube. In accordance with this invention, the above is accomplished by means of an integral plastic member which is positioned to sealingly enclose an interrupted portion of the flexible blood tube and the needle. The plastic member includes a thin-walled, frangible portion positioned to permit separation of the plastic member into two pieces by breaking of the frangible portion to expose the needle for use, and to permit the blood tube to be separated. Manually operated means are also provided for shutting off flow through the blood tube at a point on the opposite side of the plastic member from the blood bag.

1 Claim, 4 Drawing Figures

SEPARABLE INTEGRAL DONOR TUBE UTILIZING AN INTEGRAL PLASTIC MEMBER WITH TUBE CLAMP

BACKGROUND OF THE INVENTION

In U.S. Pat. No. 3,127,892, the basic concept of the separable integral donor tube is described for use in blood bags. Basically, after the blood bag has been filled, the donor tube is severed to expose a needle mounted in the bore of the upstream portion of the separated donor tube, for penetrating the latex closure of a sample tube, to provide a further blood sample from the donor through the same tube.

In accordance with this invention, a simplified, one-piece plastic member is utilized to provide the functions of the structure described in the above-cited patent. Additionally, manually operable shutoff means are provided by the same structure to prevent the flow of blood through the blood tube at undesired times. Also, the structure is tamperproof, to protect its sterile integrity.

DESCRIPTION OF THE INVENTION

This application relates to an improved, separable integral donor tube connection for a blood bag, including a blood tube communicating with the blood bag and having means for parting the blood tube and exposing an internally mounted needle carried by and communicating with the tube for penetrating a closure of a sample tube.

In accordance with this invention, the blood tube parting means are defined by an integral, plastic member which is positioned to sealingly enclose an interrupted portion of the blood tube, and also to enclose the internally-mounted needle. The plastic member includes a thin-walled, frangible portion which is positioned to permit the separation of the plastic member into two pieces by breaking of the frangible portion to expose the needle for use, and to separate the blood tube.

Also, manually operated means are provided for shutting off flow through the blood tube at a point on the opposite side of the plastic member from the blood bag.

Preferably, the flow shutoff means may include a collet member positioned on the plastic member, and closure means, actuated by manual manipulation of the collet member, to press a portion of the blood tube into collapsed, sealed configuration to prevent flow therethrough. To accomplish this, in one embodiment, the collet member may press a cam or the like to collapse the blood tube against the bottom of a trough in which the tube resides, to collapse it to shut off flow, actuated by the collet member. In another embodiment, a pair of collet-actuated clamping jaws may be used, as specifically shown herein.

Referring to the drawings.

Figure 1:
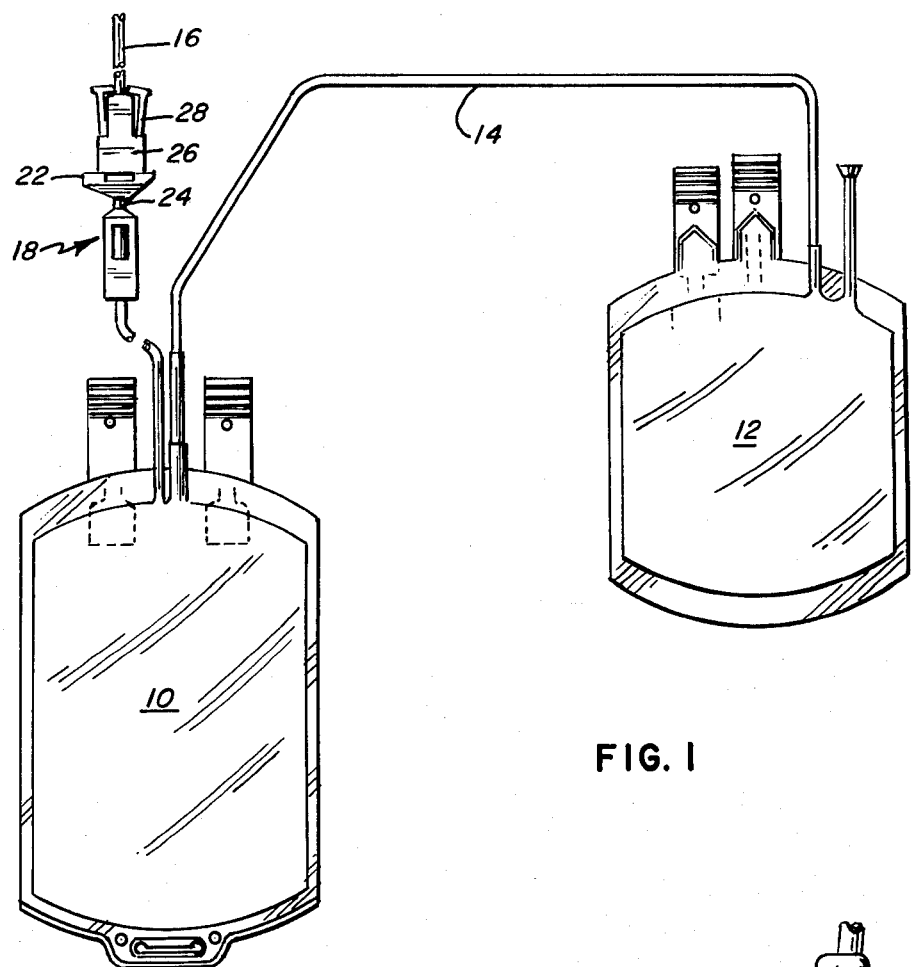
FIG. 1 is a plan view of a double blood bag system having blood donor tubing, which incorporates the invention of this application.

Referring to the drawings, a multiple blood bag system is shown comprising blood bags 10, 12 being connected by transfer tubing 14, all of which may be of the conventional construction of commercially available multiple blood bags. The donor tubing 16, which carries the usual donor needle at its end (not shown) for collection of blood, is of the separable, integral donor tube (SID) variety, and carries integral plastic member 18.

Figures 2, 3, 4:
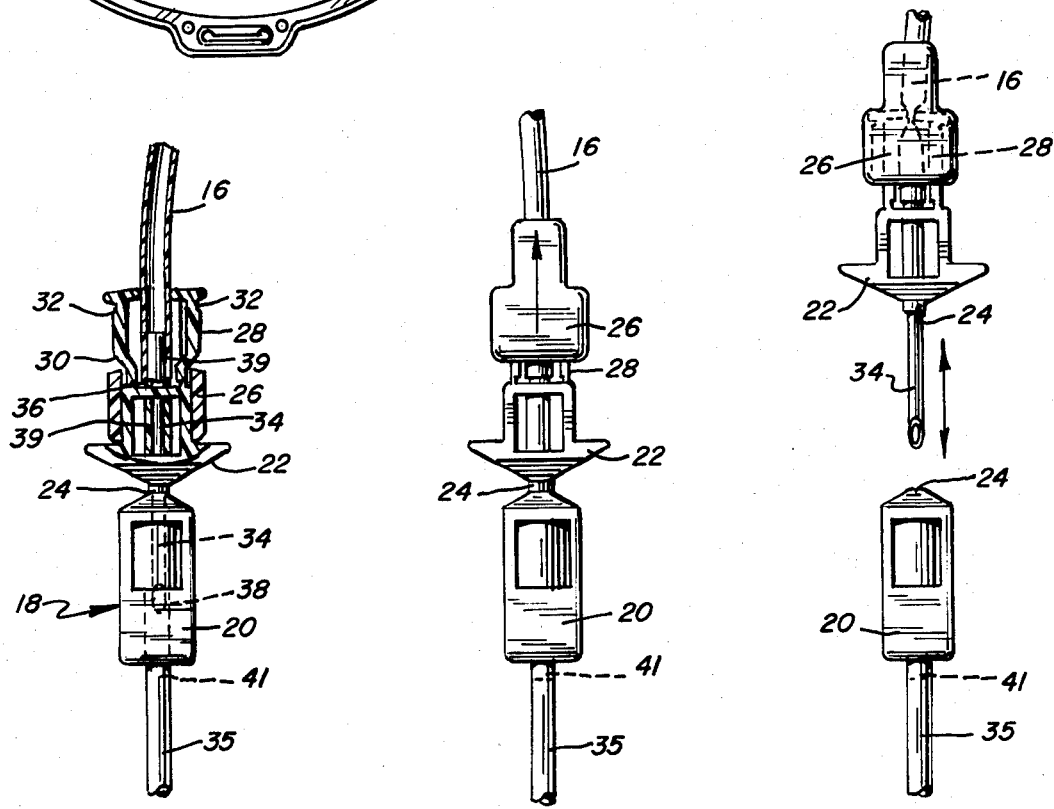
FIG. 2 is an enlarged, fragmentary view of a portion of the blood donor tube of the blood bag system of FIG. 1, taken partly in longitudinal section.
FIG. 3 is a view similar to FIG. 2, but showing the collet-actuated clamping jaws in closed position.
FIG. 4 is a view similar to that of FIG. 3, but showing the structure of this invention in separated configuration to expose the needle utilized herein.

As more specifically shown in FIGS. 2 through 4, plastic member 18 comprises first and second separable sections 20, 22 connected together by a thin, annular frangible section 24. Second section 22 carries a collet member 26, which, in turn, surrounds a pair of clamping jaws 28, which may be an integral part of section 22. Jaws 28 define outwardly projecting shoulders 30, so that when collet member 26 is manually pushing upwardly, the tips 32 of the jaws press a portion of the blood tubing 16 into collapsed, sealed configuration, to prevent flow through the tubing 16.

Blood tube 16 defines an interrupted portion between inner ends 36 and 38 of the blood tubing, both of which are sealingly carried within plastic member 18 to provide a sterile, sealed flow path for blood therethrough. Inner end 38 is defined by a bushing 41 within plastic member 38, which connects to downstream length 35 of tube 16 at its lower end. Bushing 41 is defined as part of plastic member 18, to provide sterile, sealed flow connection between tube ends 36, 38.

Needle 34 is mounted in sealing manner in member 18, within part of conduit 39, and may sealingly penetrate into the inner end 38 as well, or at least be in sealed flow communication with end 38 of the downstream length 35 of tube 16, so that a sealed flow path exists between tube ends 36, 38.

Accordingly, the device of this invention may be used in a manner which is generally similar to the prior art blood bags with SID tubing, which are at the present time commercially avaiable from the Fenwal division of Travenol Laboratories, Deerfield, Illinois.

A unit of blood may be collected in the usual manner from a donor, with the blood passing through tube 16 into blood bag 10, passing on its way through member 18 and needle 34.

After the unit of blood has been collected, collet 26 may be manually moved to the configuration shown in FIG. 3, to cause clamping jaws 28 to collapse tubing 16, to block further flow through the tubing. Then, each of first and second sections 20, 22 are manually grasped and relatively twisted to rupture annular, thin portion 24 to permit the separation of the sections and the withdrawing of needle 34 as in FIG. 3. Prior to breaking annular, thin portion 24, the portion 35 of donor tubing 16 remaining connected to blood bag 10 is sealed in a conventional manner by heat sealing or clips, to retain sterility of the contents of blood bag 10.

Needle 34 is then pessed through the latex seal of a sample collection container (not shown) and collet 26 is pushed downwardly again to reopen jaws 28, to allow blood flow to resume. As many samples as are desired may be obtained in this manner by simply raising collet 26, to close jaws 28 prior to withdrawal of the needle 34 from the sample container, and by correspondingly lowering the collet to open the flow again when the needle has passed through an injection site of a new sample container.

Thereafter, the donor needle and the portion of tubing 16 separated from blood bag 10 may be removed from the patient's arm and disposed of.

A releaseable locking detent 32 is defined on jaws 28, and a corresponding mating projecting 35 is provided upon collet 26, for releaseable interlocking, to make sure that the collet remains in its raised, flow-closing position until it is positively and forcefully withdrawn out of that position. This avoids the accidental opening of flow and consequent blood spillage.

The above has been offered for illustrative purposes only, and is not intended to limit the scope of the invention of this application, which is as defined in the claims below.

That which is claimed is:

1. In a flexible blood tube, communicating with a blood bag, means for parting said blood tube and exposing an internally mounted needle carried by and communicating with said tube for penetrating a closure of a sample tube, the improvement comprising: said means being defined by an integral plastic member, said plastic member being positioned to sealingly enclose an interrupted portion of said blood tube and said needle, a thin-walled, frangible portion of said integral plastic member positioned to permit the separation of the plastic member into two pieces by breaking of said frangible portion, to expose said needle for use and separate said blood tube, and manually operated means for shutting off flow through said blood tube at a point on the opposite side of said plastic member from said blood bag, said manually operated means including a collet member positioned on the plastic member, and clamping jaw means, actuated by manual manipulation of the collet member, to press a portion of said blood tube into collapsed, sealed configuration to prevent flow therethrough, said collet member being freely longitudinally movable along said plastic member for quick actuation, and said clamping jaw means comprising an integral component of said plastic member.

* * * * *